United States Patent
Svejk

(10) Patent No.: US 6,687,524 B1
(45) Date of Patent: Feb. 3, 2004

(54) DISPOSABLE NEONATAL ELECTRODE FOR USE IN A HIGH HUMIDITY ENVIRONMENT

(75) Inventor: Christian A. Svejk, Meriden, CT (US)

(73) Assignee: CAS Medical Systems, INC, Branford, CT (US)

( * ) Notice: Subject to any disclaimer, the term of this patent is extended or adjusted under 35 U.S.C. 154(b) by 278 days.

(21) Appl. No.: 09/382,120

(22) Filed: Aug. 24, 1999

(51) Int. Cl.[7] ................................................ A61B 5/04
(52) U.S. Cl. ...................... 600/391; 600/395; 600/397; 607/152
(58) Field of Search ................................ 600/372–393, 600/395; 607/152

(56) References Cited

U.S. PATENT DOCUMENTS

| | | | |
|---|---|---|---|
| 4,559,950 A | | 12/1985 | Vaughn et al. ............... 128/641 |
| 4,674,511 A | * | 6/1987 | Cartmell ..................... 128/640 |
| 4,694,835 A | * | 9/1987 | Strand ......................... 128/640 |
| 5,215,087 A | * | 6/1993 | Anderson et al. ........... 600/373 |
| 5,330,527 A | * | 7/1994 | Montecalvo et al. ....... 607/152 |
| 5,520,180 A | * | 5/1996 | Uy et al. ..................... 607/152 |
| 5,645,062 A | * | 7/1997 | Anderson et al. ........... 128/640 |
| 5,921,925 A | * | 7/1999 | Cartmell et al. ............ 600/391 |
| 5,924,983 A | * | 7/1999 | Takaki et al. ................ 600/372 |

FOREIGN PATENT DOCUMENTS

| | | | |
|---|---|---|---|
| EP | 95302258.9 | 10/1995 | ......... A61B/5/0448 |
| WO | PCT/US92/09329 | 5/1993 | ......... A61B/5/0408 |

* cited by examiner

Primary Examiner—Michael Peffley
Assistant Examiner—David M. Ruddy
(74) Attorney, Agent, or Firm—William W. Jones

(57) ABSTRACT

An ECT, EEG, EMG, ENG or impedance pneumography hospital electrode is designed for use on neonates in high humidity environments, such as in a high humidity incubator. The electrode includes a silver-silver/chloride sensor; a signal transmitting lead connected to the sensor; and an electrically conductive, self-adhesive gel which electrically connects the sensor to the patient's skin. The conductive, self-adhesive gel is formed from a hydrogel which is hydrophilic in nature. In order to stabilize the adhesiveness of the gel in the high humidity environment, the gel is provided with an adjunct non-hydrophilic adhesive member which provides improved adhesion to the skin while maintaining contact between the conductive gel and the patient's skin. The use of the adjunct adhesive member enables the electrode assembly to be used in the high humidity environment for extended periods of time without becoming detached from the patient's skin.

9 Claims, 2 Drawing Sheets

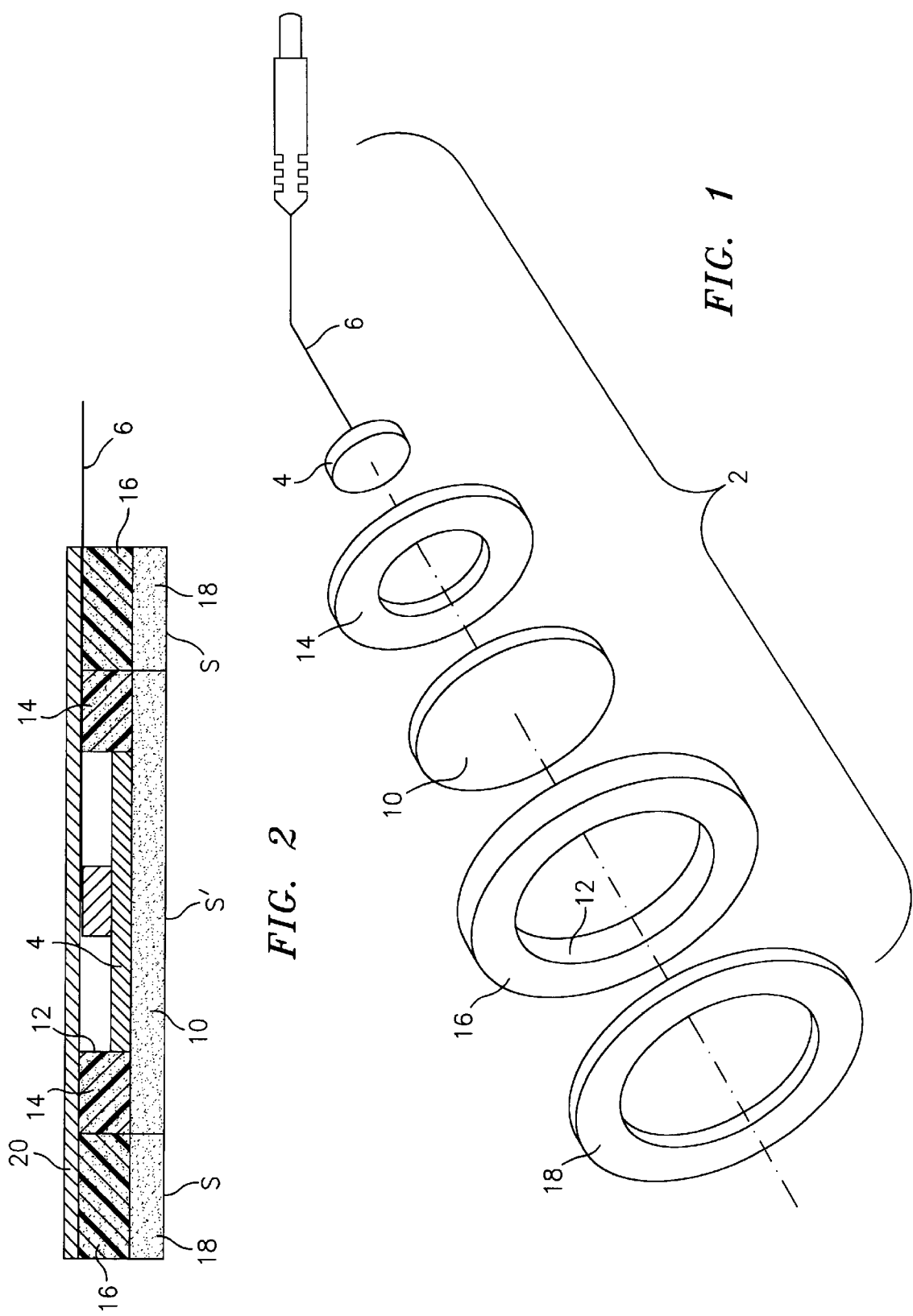

DISPOSABLE NEONATAL ELECTRODE FOR USE IN A HIGH HUMIDITY ENVIRONMENT

TECHNICAL FIELD

This invention relates to a disposable medical electrode which provides extended use in a high humidity environment. More particularly, this invention relates to an ECG, or the like, electrode which is suitable for use on neonatal patients who are placed in a high humidity incubator environment. The electrode of this invention will not prematurely disengage from the neonate's skin due to hydrogel member water absorption from the high humidity environment.

BACKGROUND ART

Medical electrodes are widely used for the measurement and monitoring of ECT, EEG, EMG, ENG and impedance pneumography in hospitals. These electrode assemblies are used for both adult and neonatal patients, and are fastened directly to the skin of the patient for sensing of the respective electrical signals emanating from the patient's body. The electrodes most widely used at the present time, include a silver-silver chloride sensor having a signal transmitting line connected thereto, and mounted in an electrically conductive, self adhesive hydrogel member. The hydrogel provides a conductive connection between the patient's skin and the sensor so that electrical signals emanating from the patient's body will be sensed by the sensor. The signal transmitting line is connected to a monitor, such as an oscilloscope, or the like, which provides a readout of the the sensed electrical signals from the patient. The electrode may necessarily be used to monitor a patient for a relatively long period of time, therefore, it is critical that the intimate contact between the patient's skin and the electrode, which is provided by the conductive, adhesive hydrogel, be stable over the monitoring period. In most environments, stability of the patient-electrode contact is not a problem, and extended monitoring utility is obtainable.

One environment which has caused problems with the aforesaid adhesion stability is a newly developed high humidity incubator environment that is used for care of neonates. A high humidity environment is becoming a preferred method for combating trans-epidermal water loss (TEWL) in low birth weight (about six hundred to about fifteen hundred grams) neonates. Due to the fact that these neonates have skin that is very underdeveloped, two problems arise. TEWL is the first. Water escapes very easily through the skin, resulting in dehydration. "Swamping" is used to combat excessive TEWL by reducing the moisture gradient between the patient and the ambient environment. By elevating the ambient humidity, water is much less likely to migrate through the skin. Secondly, the underdeveloped skin is prone to damage, leading to possible infection and death. Aggressive adhesives cannot be used on vital signs-monitoring devices due to the delicate condition of the skin.

The relative humidity in such incubators is in the range of about 50% to about 90%. The conductive, adhesive hydrogel member of the electrode, as noted above, is hydrophilic, and thus is prone to absorption of water from the highly humid atmosphere in the newly developed incubators. The result of placing the electrode hydrogel member in the high humidity environment of the aforesaid newly developed incubator is absorption of water by the hydrogel member, and subsequent erosion of the adhesiveness of the hydrogel. The electrode will thus simply fall off of the neonatal patient if left in the high humidity incubator environment for a time period which can be as short as one to two hours. It would thus be highly desirable to provide an electrode which displays extended adhesion to the skin of a neonate in the high humidity environment of the currently used incubators.

DISCLOSURE OF THE INVENTION

This invention relates to a medical electrode of the character described which has enhanced skin adhesion in a high humidity environment. The electrode of this invention includes the conventional sensor and electrical lead. A self adhesive conductive hydrogel member surrounds the sensor and serves to provide enhanced signals to the sensor. The hydrogel member is surrounded by an adjunct adhesive component which will not absorb significant amounts of water from the high humidity environment in the incubators. The adjunct adhesive component is preferably a relatively hydrophobic material and it is adhered intimately to the conductive hydrogel while allowing the conductive hydrogel to maintain its intimate contact with the neonate's skin. The adjunct adhesive component protects the conductive hydrogel member against excessive water absorption, and also enhances and stabilizes the adhesive bond between the electrode and the neonate's skin. One configuration of the adjunct adhesive component which has proven to be exemplary is an annular, or donut, shape.

Enabling but non-essential details of the invention will become more readily apparent from the following detailed description of the invention when taken in conjunction with the accompanying drawings in which:

BRIEF DESCRIPTION OF THE DRAWINGS

FIG. 1 is an exploded view of one embodiment of an electrode formed in accordance with this invention;

FIG. 2 is a fragmented sectional view of the electrode of FIG. 1; and

DETAILED DESCRIPTION THE INVENTION

Figure 3:
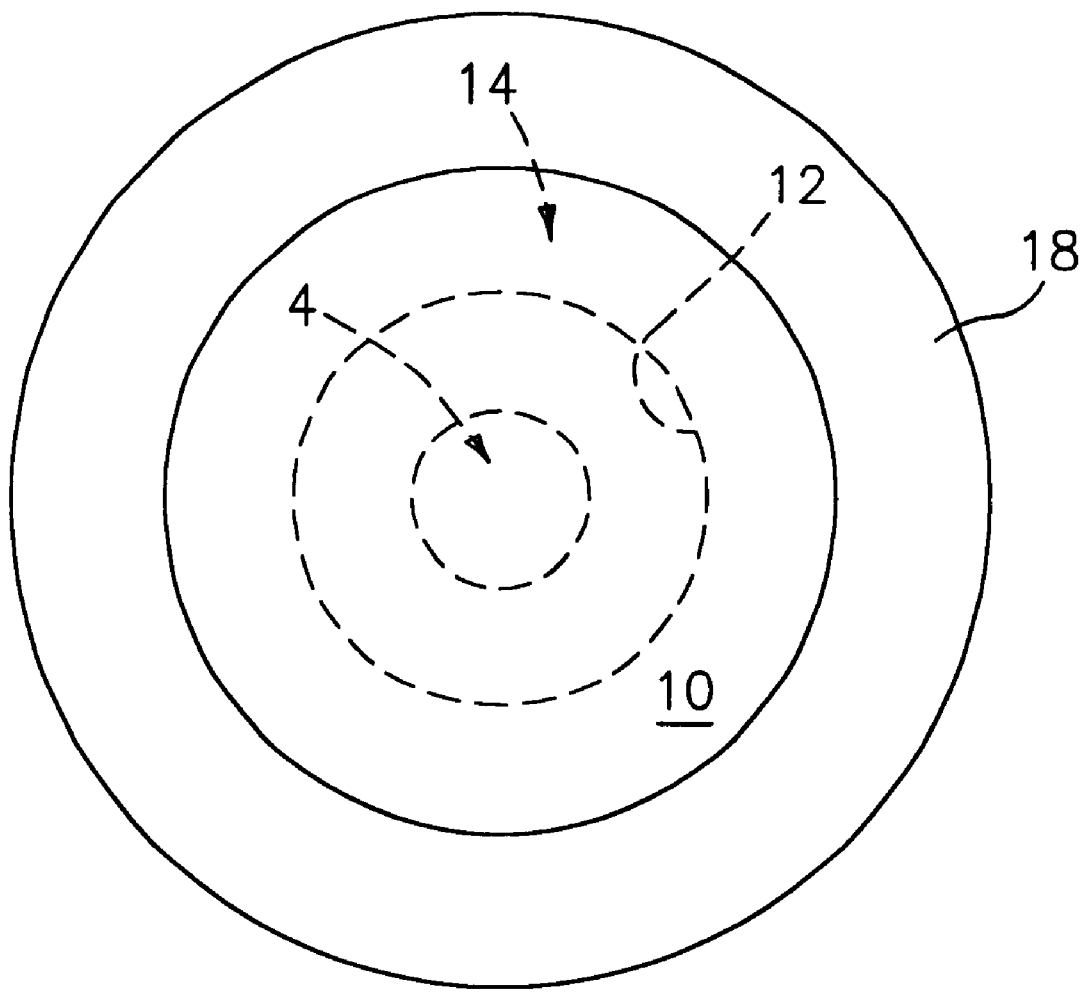
FIG. 3 is a plan view of the skin-contacting side of the electrode of FIG. 1.

Referring now to the drawings, there is shown in FIG. 1 an exploded view of one embodiment of an electrode denoted generally by the numeral 2, which has been formed in accordance with this invention. The electrode 2 includes an Ag/AgCl sensor 4 which is coupled to a signal transmission wire 6 having a distal plug 8 for connection to a standard yoke cable (not shown). A disc-shaped electrically conductive and self-adhesive hydrogel member 10 contacts the sensor 4 and provides electrical contact between the sensor 4 and the patient's skin. The hydrogel member 10 is secured to a first annular foam ring 14 which forms a recess 12 for reception of the sensor 4. A second annular foam ring 16 surrounds the first foam ring 14 and is adhered to an adjunct adhesive ring 18 which, in turn, surrounds the hydrogel member 10. The adjunct adhesive ring 18 is not significantly hydrophilic, and is essentially non-conductive. Its function is as an adhesive to prevent the hydrogel member 10 from prematurely losing electrical contact with the patient's skin. The use of such an adjunct adhesive member in the electrode 2 has resulted in a markedly improved adherence of the electrode 2 to the neonate's skin in the above-described incubator swamping environment.

Referring now to FIG. 2, there is shown a cross-sectional view of the patient's skin-contacting portion of the electrode 2. It will be noted that the skin-contacting surface S of the adhesive ring 18, and the skin-contacting surface S' of the hydrogel member 10, are co-planar, so that both of these surfaces will intimately contact the skin of the neonatal patient being monitored. Due to the presence of the ring 18, absorption by the hydrogel member 10 of sufficient water from the incubator atmosphere which causes a degree of swelling of the hydrogel 10 that would result in loss of adhesive capability in the hydrogel 10 will not adversely effect the performance of the electrode 2. Thus, the inclusion of the adjunct adhesive ring 18, which will not absorb significant amounts of water from the incubator atmosphere, ensures extended electrode-to-patient-skin adherence. The adjunct adhesive ring 18 ensures that the electrode 2 will remain adhered to the neonate's skin for a period of time of at least five days in the high humidity swamping incubator environment. As seen in FIG. 2, a cover layer 20 of adhesive paper preferably serves to bond the foam rings 14 and 16 to each other, and protects the sensor 4 from exposure to the humid atmosphere in the incubator.

Referring now to FIG. 3, it will be noted that the annular adhesive ring 18 extends to the periphery of the hydrogel member 10 so as to provide a strong and intimate complete peripheral bond between the neonate's skin and the electrode 2. The ring 18 thus provides enhanced and stable adhesion of the electrode 2 to the neonate's skin. The combination of the adhesive disc 18 with the adhesive and electrically conductive hydrogel member 10 in the electrode 2 ensures prolonged adhesion of the electrode 2 to the neonate's skin along with acceptable signal transmission from the hydrogel member 10 to the sensor 4.

The self adhesive and electrically conductive hydrogel 10 can be formed from the hydrogel which is a product of the Ludlow Corporation of Two Ludlow Park Dr., Chicopee, Mass.; and the self adhesive non-conductive ring can be formed from a hydrocolloid which is a product of Avery Dennison, 250 Chester Street, Painesville, Ohio.

Since many changes and variations of the disclosed embodiment of the invention may be made without departing from the inventive concept, it is not intended to limit the invention otherwise than as required by the appended claims.

What is claimed is:

1. A medical electrode for use in a high relative humidity neonatal care environment, said electrode assembly comprising:
    a) a sensor for sensing electrical signals emanating from a patient's body;
    b) a hydrophilic self adhesive electrically conductive hydrogel member contacting said sensor, said hydrogel member having a surface which contacts a patient's skin and said hydrogel member being operable to transmit electrical signals from the patient's skin to said sensor; and
    c) an adjunct self adhesive non-electrically conductive securement member adjacent to and connected to said hydrogel member, said securement member having a skin-contacting surface which is coextensive with hydrogel member surface, the adhesive nature of said adjunct member being essentially unaffected by high humidity whereby said adjunct member provides extended securement of the electrode to a patient's skin in the high humidity environment after said hydrogel member has essentially lost its self adhesiveness due to water absorption.

2. The medical electrode of claim 1 wherein said adjunct member maintains its adhesiveness in environments having a relative humidity of up to about 90%.

3. The medical electrode of claim 1 wherein said hydrogel member loses its self adhesiveness during use in an environment have a relative humidity of more than about 50% due to water absorption from the environment.

4. The medical electrode of claim 1 wherein said hydrogel member and said adjunct member are laminated to concentric foam rings which are connected to each other.

5. The medical electrode of claim 4 wherein said hydrogel member foam ring is disposed inwardly of said adjunct member foam ring.

6. The medical electrode of claim 5 wherein said hydrogel member and said hydrogel member foam ring combine to form a pocket in which said sensor is positioned.

7. The medical electrode of claim 6 wherein said foam rings are connected together by an adherent cover sheet.

8. In a medical electrode of the type having an electrical signal sensor and a self adhesive and electrically conductive hydrophilic hydrogel member having a skin-contacting surface, which hydrogel member is connected to the sensor for transmitting electrical signals from a patient's skin to the sensor, the improvement comprising an adjunct adhesive member which surrounds the hydrogel member and has an adjunct skin-contacting surface which is coextensive with the hydrogel member skin-contacting surface, said adjunct member being able to retain its adhesiveness in environments having a relative humidity of more than about 50% so as to maintain adhesion to a patient's skin after the hydrogel member has essentially lost its adhesiveness due to water absorption for the humid environment.

9. The medical electrode of claim 8 wherein said adjunct member will retain its adhesiveness in an environment having a relative humidity of up to about 90% for an extended time period during which the hydrogel member will have lost its adhesiveness due to absorption of water from the humid environment.

* * * * *